(12) United States Patent
Rouquette

(10) Patent No.: US 9,788,797 B2
(45) Date of Patent: Oct. 17, 2017

(54) EXERCISE-ASSISTING DEVICE FOR FORECASTING THE CHANGE IN A PHYSIOLOGICAL PARAMETER AS A FUNCTION OF AN ITINERARY

(75) Inventor: Sebastien Rouquette, Castanet-Tolosan (FR)

(73) Assignee: CENTRE NATIONAL D'ETUDES SPATIALES (CNES), Paris (FR)

( * ) Notice: Subject to any disclaimer, the term of this patent is extended or adjusted under 35 U.S.C. 154(b) by 1063 days.

(21) Appl. No.: 13/988,154

(22) PCT Filed: Nov. 17, 2011

(86) PCT No.: PCT/FR2011/052683
§ 371 (c)(1),
(2), (4) Date: May 17, 2013

(87) PCT Pub. No.: WO2012/066249
PCT Pub. Date: May 24, 2012

(65) Prior Publication Data
US 2013/0237778 A1 Sep. 12, 2013

(30) Foreign Application Priority Data

Nov. 19, 2010 (FR) ...................................... 10 04509

(51) Int. Cl.
*A61B 5/00* (2006.01)
*A63B 71/00* (2006.01)
(Continued)

(52) U.S. Cl.
CPC .......... *A61B 5/7275* (2013.01); *A61B 5/0002* (2013.01); *A61B 5/0022* (2013.01);
(Continued)

(58) Field of Classification Search
CPC . A61B 5/0002; A61B 5/1118; A61B 5/02055; A61B 5/02438; A61B 5/681;
(Continued)

(56) References Cited

U.S. PATENT DOCUMENTS 7,534,206 B1 5/2009 Lovitt et al.
2004/0046692 A1 3/2004 Robson et al.
(Continued)

FOREIGN PATENT DOCUMENTS

EP 1 691 170 A1 8/2006

OTHER PUBLICATIONS

"A dynamic heart rate prediction model for training optimization in cycling (P83)", Ankang Le, Thomas Jaitner, Frank Tobias, Lothar Litz, Bicycle, Modelling,The Engineering of Sport 7, vol. 1, springer Paris, pp. 426-433.
(Continued)

*Primary Examiner* — Timothy J Neal
*Assistant Examiner* — Aaron B Fairchild
(74) *Attorney, Agent, or Firm* — Young & Thompson

(57) ABSTRACT

A device (1) for assisting with physical exertion management, includes a physiological sensor, a positioning device, at least one memory in which data representative of the itinerary to be travelled during the physical exertion can be recorded, and at least one data processing unit organised so as to produce forecast data representative of the change in an physical exertion parameter over the remaining itinerary to be travelled by the individual, to compare these forecast data with predetermined data, and to produce and transmit a message, the content of which depends on the result of the comparison of the forecast data and the predetermined data, with a view to communicating the message to a user.

11 Claims, 4 Drawing Sheets

(51) Int. Cl.
*A61B 5/024* (2006.01)
*A61B 5/11* (2006.01)
*A61B 5/01* (2006.01)
*A61B 5/0205* (2006.01)
*A61B 5/145* (2006.01)
*A63B 24/00* (2006.01)

(52) U.S. Cl.
CPC ............ *A61B 5/01* (2013.01); *A61B 5/02055* (2013.01); *A61B 5/02438* (2013.01); *A61B 5/1112* (2013.01); *A61B 5/1118* (2013.01); *A61B 5/14532* (2013.01); *A61B 5/14542* (2013.01); *A61B 5/4866* (2013.01); *A61B 5/681* (2013.01); *A61B 5/7246* (2013.01); *A61B 5/742* (2013.01); *A63B 24/0062* (2013.01); *A63B 2024/0068* (2013.01)

(58) Field of Classification Search
CPC ... A61B 5/7275; A61B 5/6813–5/6817; A61B 5/6801–5/6829; A61B 5/4866; A61B 5/00; A61B 5/01; A61B 5/0205; A61B 5/145; A61B 5/11; A63B 24/0062; A63B 24/50; A63B 24/04
USPC .......................... 600/301, 323, 483; 482/8, 9
See application file for complete search history.

(56) References Cited

U.S. PATENT DOCUMENTS

| | | | |
|---|---|---|---|
| 2006/0004265 A1* | 1/2006 | Pulkkinen | A61B 5/0205 |
| | | | 600/300 |
| 2008/0009275 A1 | 1/2008 | Werner et al. | |
| 2008/0109158 A1 | 5/2008 | Huhtala et al. | |

OTHER PUBLICATIONS

"Physiologie du sport et de l'exercice : Adaptations physiologiques a l'exercice physique", Jack H., Wilmore, David L. Costill, transl. Arlette Delamarche, Paul Delamarche et Carole Groussard, De Boeck Universite, 2006, pp. 477-491.
"Precis de physiologie de l'exercice musculaire", Per-Olof Astrand et Kaare Rodahl, Editions Masson, 3e ed., 1994.
International Search Report, dated Mar. 14, 2012, from corresponding PCT application.

* cited by examiner

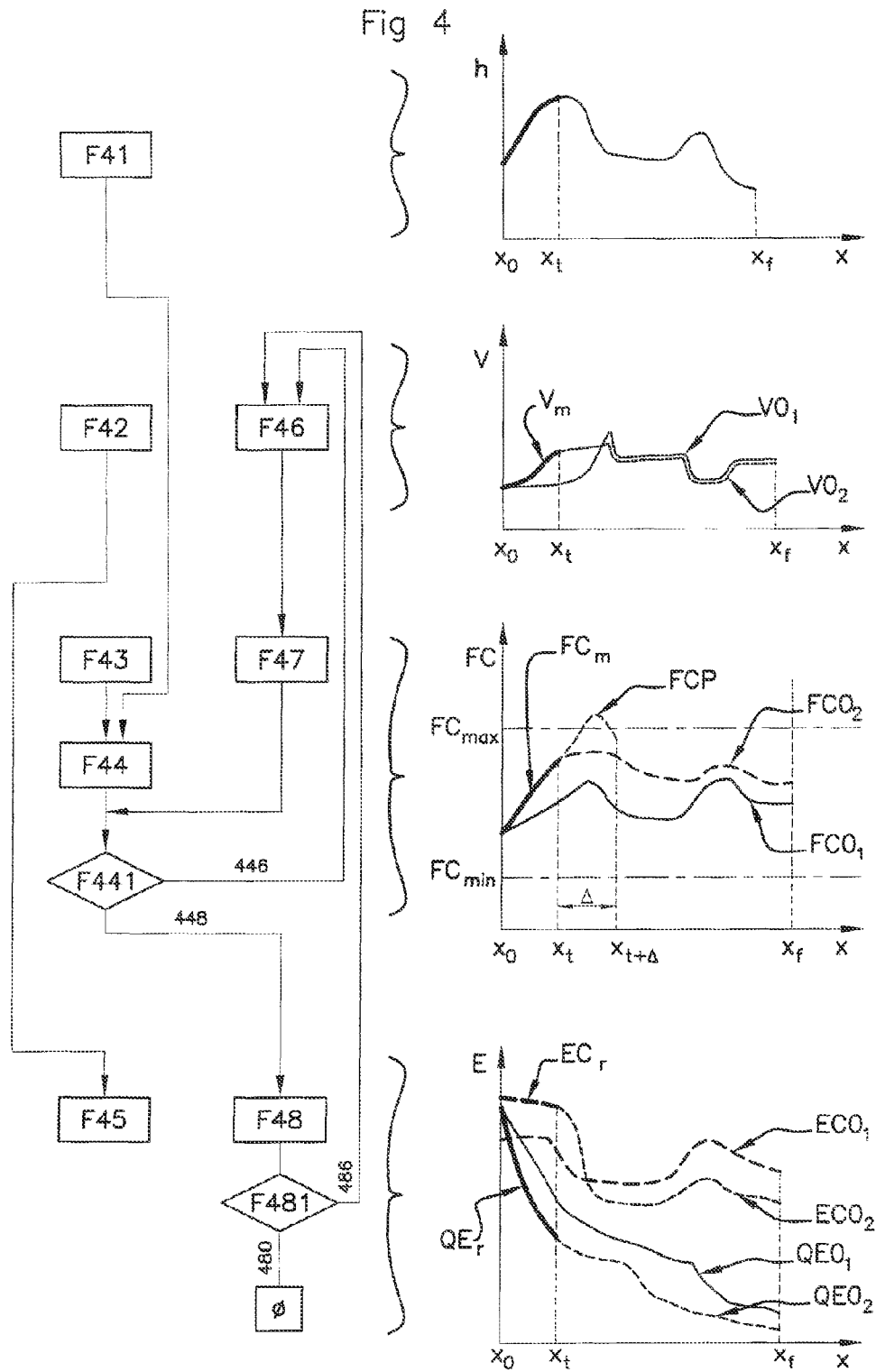

EXERCISE-ASSISTING DEVICE FOR FORECASTING THE CHANGE IN A PHYSIOLOGICAL PARAMETER AS A FUNCTION OF AN ITINERARY

BACKGROUND OF THE INVENTION

Field of the Invention

The invention concerns a device enabling management of the physical exertion of a human being or of an animal over a predetermined itinerary. Throughout the following, "subject" designates any human being or animal on which such a device is used in order to forecast at least one of his/her physiological parameters.

The user of such a device may be the subject himself/herself (commonly when the subject is a human being) or a person who is not the subject (the case of a human user who wishes to monitor the exertion of an animal).

In many situations it is advantageous to be able to assist the management, and in particular to monitor and forecast, the physical exertion of a subject.

A physical exertion is provided in numerous situations. For example, a subject in rehabilitation following a traumatism or an operation may have to perform physical exercises requiring only a moderate exertion. It is therefore advantageous to be able to assist the management and avert an exertion deemed too great for a subject undergoing rehabilitation. Conversely, situations where the physical exertion to be provided is at a high level, such as in the course of training or in the course of sport competitions, require a significant physical exertion that one may wish to monitor and/or optimise. In addition, the physical exertion may be constituted largely by stress, for example in the course of a flight in a glider or in the course of a motor race.

The organism of a subject regulates its physiological parameters to the utmost of its capabilities with the aim of protecting itself. Therefore, the variation of these physiological parameters and their evolution reflect the physiological and physical state of a subject. For example, the oxygen saturation of the blood is a very good indicator of the physical state of a subject.

The heart rate (in French, Fréquence Cardiaque (FC)) is another very reliable physiological parameter as regards the state of the organism of a subject. Thus a higher heart rate generally indicates a more advanced level of hypoxia.

Description of the Related Art

On this subject, we know the document "A dynamic heart rate model for training optimization in cycling (P83)," Ankang Le, Thomas Jaitner, Frank Tobias, Lothar Litz, in *The Engineering of Sport* 7, ed. Springer Paris, which describes a device enabling the rate of heartbeat of cyclists on exercise bikes, which impose a given power on the cyclist, to be collected and forecasted prior to a training session.

However, the subject of such a device is unable to move over a real itinerary which, by definition, is much more complex than any simulation imposed by an exercise bike.

Moreover, it is therefore impossible for the user of the device to make choices in real time about the pace of the subject, because he/she cannot regularly re-evaluate what the future exertions to be provided by the subject will be, and if the exertion that said subject is providing at a time t is compatible with the rest of an itinerary to be travelled.

There is therefore a need for a device that is capable not only of gathering, recording and displaying physiological parameters relating to a subject, be it animal or human, but also of forecasting them over at least a portion of a route remaining to be travelled over a predetermined itinerary, in particular as a function of the position of the subject over this itinerary.

Moreover, there is a need for such a device that is portable, so that a subject can take it with him/her over a real itinerary and can have at his/her disposal an aid for the management of his/her exertion at all points of his/her journey, in real time and autonomously.

BRIEF SUMMARY OF THE INVENTION

The present invention therefore aims generally to solve the problem of the forecasting of one or more physiological parameters as a function of a route remaining to be travelled by a subject over a predetermined real itinerary.

The invention aims, more particularly, to propose a device enabling the evolution of one or more physiological parameters to be predicted as a function of the route remaining to be travelled by a subject over a predetermined itinerary.

Within this context, the invention aims, in particular, to forecast at least the rate of heartbeat of the subject over at least one time-interval or distance-interval from at least one point of a route remaining to be travelled.

The invention is also directed towards a device that is portable and autonomous, in order to provide complete autonomy of the subject over a real itinerary.

The invention also aims to provide a device that is capable of refining forecasts of exertion parameters as a function of environmental factors such as, in particular, weather factors.

The invention also aims to provide a device that is capable of forecasting other physiological parameters of the subject, such as, for example, the oximetry, the temperature, the energy consumed and the remaining energy.

The invention aims, in particular, to provide a device for assisting the management of a physical exertion, said device being capable of being utilised just as well for an animal as for a human being.

The invention also aims to provide a device for assisting the management of a physical exertion relating to rehabilitation, training or a sporting competition.

The invention aims to provide a device for assisting the management of a physical exertion that is applicable to all types of physical exertion, and in particular in all kinds of sport.

In order to do this, the invention concerns a portable device for assisting the management of a physical exertion provided by a subject, comprising:
  at least one sensor for a physiological parameter, called exertion parameter, evolving as a function of the physical exertion, said sensor being suitable to provide digital data, called exertion data, that are representative of said exertion parameter,
  at least one device, called positioning device, that is suitable to determine its own position in a given topographical frame of reference and to provide digital data, called positioning data, that are representative of this position,
  at least one interface for communication with a user,
  at least one memory in which data, called input data, are capable of being recorded, comprising at least:
    positioning data provided by said positioning device,
    exertion data,
    data that are representative of an itinerary to be travelled in said topographical frame of reference by said subject in the course of the physical exertion, at least one data-processing unit, designed:
- to generate data, called forecast data, that are representative of the evolution of at least one exertion parameter over the itinerary remaining to be travelled by the subject, as a function of the input data, from equations and tables of values recorded in at least one memory of the device,
- to compare these forecast data with predetermined values recorded in at least one memory of said assistance device,
- to generate data that are representative of a message, the content of which is a function of the result of the comparison of the forecast data and the predetermined values,
- to transmit said data that are representative of a message to the interface, with a view to the communication of said message to a user.

The invention is applicable to any subject belonging to the animal kingdom in the biological sense of the term. That is to say, the subject may be an animal in the common sense of the term, or a human being.

It is to be noted, however, that the user of the device according to the invention may be distinct from the subject. In the case where the subject is a horse, for example, the user of the device may be the rider. Likewise, an athlete may be the subject, and his/her coach may be the user.

A device according to the invention is at least partly portable, in particular, at least the load sensors have to be dimensioned so as to be able to be worn by the subject.

The portability of such a device comes in useful when it is a question of using it on a subject that does not have a vehicle—that is to say, in particular for non-motorised sports or physical activities (walking, running, cycling, swimming, horse-riding, etc.). Such a device has to be portable in the sense that it is easily carried by a subject in the course of making a physical exertion without any relationship with the fact of carrying the device. Such a device must therefore present a much lower weight than the weight of the individual (for example, about a hundred grams at most for a human being) and relatively reduced dimensions in comparison with the subject (for example, 100 mm×60 mm×30 mm for a human being). Ideally, the device is light enough and small enough to be worn by a subject during his/her physical exertions without the fact of wearing the device having an influence, in well-known manner, on the physical performance of the subject during his/her exertion. For example, the device may take the form of a bracelet to be worn on the wrist for a human subject.

A device according to the invention can be used in diverse situations of physical exertion. Thus the invention can be applied to a device intended to assist the rehabilitation of subjects following an operation and/or a traumatism. Said device can also be used in sporting situations, in training or in competition.

Furthermore, the activities in which a device according to the invention is applicable are highly varied. All activities involving a physical exertion, be it intense or not, can justify the use of a device according to the invention. There is nothing to prevent, for example, using it in sporting events of autosport type, in order to monitor and forecast one or more physiological parameters or the physical state and/or the general fatigue state of a driver. There is nothing, either, to prevent applying the invention in fields where the management of the stress of the subject is important, for example in gliding competitions or paragliding competitions.

In particular, a single device according to the invention is not dedicated to a unique type of physical exertion. Such a device is designed to be able to provide forecast data in numerous types of physical exertion. For example, such a device can be used regularly and indiscriminately for running, cycling, swimming. For instance, a subject going in for the triathlon will be able to use the same device throughout the sporting event, possibly by indicating to the device a change of mode of physical exertion with the aid of an interface. Advantageously, a user profile will already be known to the device when the user takes up a new type of physical exertion, and the forecasts will be even more precise, without prior learning of the device about this type of exertion.

The exertion data, itinerary data, forecast data, positioning data are digital data that are representative of values. For instance, the term "forecast values" or "programmed values" will be used in the following to designate the different types of values represented by the "forecast data".

Moreover, a device according to the invention includes physiological sensors that are suitable to convert a physiological parameter that is capable of being modified at the time of a physical exertion, in particular as a function of the intensity of the physical exertion, into digital data that are representative of the measurement carried out. For example, and advantageously, such a physiological sensor can convert the rate of heartbeat of a subject into digital data. It goes without saying that different types of sensors based on different types of technologies (audio, optical, thermal, etc.) may be chosen, depending on their known advantages for each of the exertion parameters to be measured.

A positioning device according to the invention enables positioning data to be provided in real time relating to the position of a device according to the invention, and therefore to the position of the subject when he/she is in proximity to said device. This position advantageously comprises three items of positioning data: latitude, longitude and altitude. These data relate to the environment in which the subject is located: on Earth or on another celestial body in the solar system, in a cave, etc.

The geo-positioning data enable, in particular, the energy expenditure to be calculated as a function of the journey. Thus, the difference in height gives an indication of the potential energy that the subject will have to provide.

A positioning device according to the invention may use various types of position-finding technologies. In particular, a positioning device according to the invention is suitable to triangulate data transmitted by the satellites of a worldwide positioning system (GPS, Galileo, etc.). Said positioning device may alternatively, or in combination, determine its position from a network of antennas, for example of mobile-telephony type (GSM, etc.). Lastly, a positioning device may, on its own or in combination with the technologies previously described, determine its position with the aid of the calculation of the displacements achieved from a certain known position. In this latter case, knowledge of the displacements involves measuring the changes of trajectory, for example with the aid of an accelerometer, the speed of displacement of the subject, and the time that has elapsed between each change of trajectory. Other position-finding means may be envisaged in accordance with the invention, on their own or in combination with the means previously described.

A positioning device according to the invention relates to a positioning and is designed to operate on real journeys—that is to say, journeys to be found outdoors (roads, paths, unmarked itineraries, etc.). Such a device is not applicable within the context of virtual journeys simulated on indoor training machines.

A positioning device according to the invention is suitable to access and read maps, in particular in the form of files. The maps may be recorded in memory or downloaded from a remote device. In particular, the maps may be in the form of one or more separate files.

Moreover, a positioning device according to the invention is designed to calculate an itinerary between a first position, in particular its own position, and a second position, for example provided as input datum by a user of the assistance device. Such a device is designed to be able to calculate an itinerary in accordance with one or more criteria (journey-time, minimum total difference in height, distance, etc.) to be optimised.

A positioning device according to the invention is suitable to provide at least an altimetrical representation of the itinerary to be travelled. In fact, the relief information (positive gradients, negative gradients, plateaus) is necessary for the forecasting of physiological parameters of the subject, at least when he/she is moving on the ground.

In addition, a positioning device according to the invention is suitable to update an itinerary in real time as a function of a measured position which is evolving.

In addition, a device according to the invention advantageously includes an interface that is suitable for a human user.

The interface may be realised in accordance with several methods of communication with the human user: optical (for example, a screen), acoustic (for example, an audio-alarm device), haptic (for example, a device that is suitable to transmit a sensation to a finger), a combination of these means, or some other method. Thus a interface may be a simple means of communication, wired or wireless, enabling the device to send and/or receive information to/from another device.

The interface with a user enables the user to interact with the device. In particular, said interface enables the device to be adjusted in accordance with the various modes of operation integrated into the device.

For example, a device according to the invention may advantageously propose to a user a choice of a sport and a mode of physical exertion, for example a "rehabilitation" mode, a "training" mode or a "competition" mode. These input data enable said device to select the equations and/or charts to be used and the threshold values (or ranges) to be set.

An interface of a device according to the invention also enables the user to program the itinerary that the subject will travel.

In addition, in the case of a device that is capable of making forecasts relating to several physiological parameters the interface can enable the user to choose which physiological parameters he/she wishes the device to forecast and/or display. There is nothing to prevent making provision that the user is also able to choose different modes of representation of the forecast data: graphical or digital, according to a sampling which is a function of the time or of the distance (sliding average, instantaneous values, etc.). Moreover, a device according to the invention includes memories, the technology of which is chosen to accord to the technical characteristics expected of such a memory (persistence, read/write speed, capacity, etc.). Such memories are suitable to store positioning data, exertion data relating to physiological parameters, itinerary data in the same topographical frame of reference as the positioning data. Advantageously and in accordance with the invention, such memories are designed also to store other types of data: formulae and charts that are useful for the operations carried out by the processing unit, and/or others.

A data-processing unit according to the invention advantageously includes at least one processor, and possibly means for storage of internal data (volatile memory, non-volatile memory etc.). A data-processing unit in a device according to the invention is designed to be able to receive and process the digital data stemming from the physiological sensor(s), from the positioning device and from the device for calculating itineraries, and/or to retrieve these data from said memories of the device and/or its own internal memories.

In particular, a processing unit according to the invention is designed to implement at least the following five steps:
a) accessing input data recorded in at least one memory, amongst which data are:
   positioning data,
   data that are representative of an exertion parameter in this position,
   data that are representative of a route remaining to be travelled along the itinerary to be travelled,
b) applying biological and/or mechanical equations and/or charts, depending on the type of exertion and/or on the subject, to these data in order to generate forecast data that are representative of the future evolution of at least one exertion parameter,
c) comparing these forecast data to predetermined values, in particular recorded in a memory, said predetermined values having been keyed in manually by a user or calculated by the data-processing unit,
d) generating data that are representative of a message as a function of the result of step c), in particular generating data that are representative of a piece of advice or of an alarm sent to a user of the device if at least one exertion parameter is above or below predetermined values,
e) transmitting said data that are representative of a message to said interface, in order that the information content of the message can be understood by a user.

In particular, step a) can be performed by accessing data stored in volatile memory coming directly from, respectively, the positioning device, the physiological sensor, and the device for calculating an itinerary.

From the input data cited previously, the data-processing unit is suitable to determine secondary data, in particular with the aid of a historical record of the input data. For example, the data-processing unit is suitable to determine, from historical and current position data, an instantaneous speed and/or an average speed of displacement of the subject.

The algorithm implemented by the data-processing unit in order to perform the calculation of the forecast of the rate of heartbeat is preferably of iterative type, for example a neural network. The instantaneous data are compared at each time-step to target values (objectives) related to reference values (chart) and with geo-positioning and environmental data. Such an algorithm may, for example, include the following steps:
   calculation of an average of the physiological parameters since the start of the journey at predetermined time-intervals or distance-intervals,
   measurement of discrepancy between measured real values and the programmed values calculated by the system as reference data, in order to optimise the physical exertion over the itinerary to be travelled, from the profile of the subject, from charts and from itinerary data, adaptation of the programmed values (for example, heart rate, speed) over the rest of the circuit, as a function of the discrepancies between the measured values of the physiological parameters (heart rate, SaO2, temperature, . . . ) and the target values or the warning thresholds.

The biological and/or mechanical equations and charts that are used for the prediction of physiological parameters can be chosen as a function of the type of exertion (in particular, as a function of the sport) and as a function of the subject. Such charts are available in the literature.

Moreover, the constants of certain equations may be adapted after each physical exertion, in order to represent the subject better. It may also be proposed to the user to enter manually specific characteristics of the subject (weight, height, age, sex, etc.) which are then saved by the device.

Advantageously, the forecasting of an exertion parameter is carried out with a minimal precision which depends on the parameter (for example, of the order of ±5 bpm for the heart rate, ±2% for the oxygen saturation SaO2, etc.).

In addition, depending on the calculated exertion parameters, the forecasting horizon—that is to say, the maximal duration/distance for which it is useful to make a forecast of said parameter—may be different. So, for exertion parameters known as "short-term"—that is to say, that are easily and quickly (of the order of a few minutes) modified by changes of pace, by changing environmental conditions, etc.—the forecasting horizon is relatively short: it is sufficient that the device estimates this parameter only over a few units of time/distance. For example, the heart rate can be estimated with a horizon of about ten minutes. Above that, the forecasts are highly dependent on the other parameters. For example, for a subject whose heart rate is too high it is possible to make it come down again in a few minutes without affecting its ability to come back up again later to a high heart rate.

On the other hand, other parameters may be considered as "long-term" parameters. These are parameters that can be estimated up until the end of the physical exertion, because they are less easily modified. For example, the energy consumed by a subject cannot be recovered, neither in a few minutes nor in a few hours, so long as the subject does not ingest any food. The forecasting horizon of a "long-term" parameter may therefore be extended up until the end of the physical exertion.

Thus a device according to the invention calculates values, called programmed values, for "short-term" parameters (speed, heart rate, . . . ) and "long-term" parameters (e.g. energy stored, amount of water, etc.) before the start of the exertion, over the whole of the itinerary. These programmed values correspond to an optimisation of the exertion to be provided by the subject along the itinerary as a function of, in particular, the characteristics of the subject, the mode of physical exertion, the topology of the itinerary, and possibly environmental parameters. Numerous other parameters can be taken into account in the calculation of these programmed values.

Moreover, as the subject progresses over the itinerary the device calculates forecast values with a more restricted horizon (for example, 10 minutes) for the "short-term" parameters (for example, the heart rate). These forecast values correspond to an estimation of the future evolution of the physiological parameters constituting the object of a prediction as a function of the present measured values (and possibly past measured values), of the topology of the itinerary to come immediately, and possibly of environmental parameters. Numerous other parameters can be taken into account in the calculation of these forecast values.

The measured values and the forecast values are compared in real time with the programmed values. They are also compared to threshold values (for example, a value of heart rate that is never to be exceeded).

Moreover, a device according to the invention is designed to re-analyse all of the parameters regularly and to generate at regular time-intervals new programmed values as a function, in particular, of the past values over the portion of itinerary already travelled. This enables, in particular, the optimal performance of the subject on a route remaining to be travelled to be re-evaluated as a function of underperformance or overperformance of the portion of itinerary already travelled.

Advantageously and in accordance with the invention, a first exertion parameter is the heart rate, and at least one second exertion parameter is chosen from: the oxygen saturation of the blood, the body temperature, the level of glucose in the blood, the blood pressure, the respiratory rate, the conductivity of the skin.

The heart rate is an exertion parameter that is both simple to measure and very representative of the physical state of a subject. It is therefore essential to measure the heart rate in a device according to the invention.

But a more exhaustive analysis and a more precise forecast of the performance and the resources of a subject necessitate having measurements of other exertion parameters (or physiological parameters) available. Indeed, the heart rate is not sufficient to obtain reliable and complete information on the state of the organism from the point of view of its instantaneous metabolism.

Thus the oxygen saturation of the blood—measured, for example, by a saturometer or oximeter—is a very important and necessary parameter so that a device according to the invention is suitable to forecast, for example, the fatigue state or the amount of energy that will be used by the subject over the route remaining to be travelled. Although optional, this measure is useful for the evaluation of the physical state of the subject and for the calculation of the energy consumption of the subject during the exertion.

Other physiological parameters may replace or be added to the measurement of the oxygen saturation of the blood, depending on the expected nature and accuracy of the forecast data provided by a device according to the invention. Thus a device according to the invention may include physiological sensors intended to convert into digital data physiological parameters such as: the level of glucose in the blood, the blood pressure, the body temperature, the respiratory rate, the conductivity of the skin (enabling, in particular, the sudation and therefore the loss of water to be measured), or others.

These sensors in a device according to the invention aim to ensure a more comprehensive monitoring of the physical state of the subject, and therefore to refine forecast data such as rate of heartbeat, energy consumed, water reserves, etc., in precision.

A device according to the invention is not restricted to the cited physiological sensors and may include secondary physiological sensors that are suitable to measure other physiological parameters. These measurements may be useful to refine the calculation of certain forecast data. Thus the oxygen saturation of the blood can help to forecast the future rate of heartbeat. Likewise, the oxygen saturation enables the physical state of the subject and the efficiency of energy production by the organism to be evaluated, and therefore enables the level and the evolution of the overall performance in the course of the physical exertion to be estimated (cf., for example, "Physiologie du sport et de l'exercice: Adaptations physiologiques á l'exercice physique", Jack H. Wilmore, David L. Costill, transl. Arlette Delamarche, Paul Delamarche et Carole Groussard, *De Boeck Université*, 2006).

The calculation of the forecast data can take the various measured parameters into account, separately or in interaction. That is to say, according to the equations and/or charts (which depend, in particular, on the type of exertion) applied to the measured parameters, these latter may be taken into consideration, one after the other, in order to arrive at the forecast data, or they may be taken into consideration together when they interfere with one another.

Moreover, advantageously and in accordance with the invention, said data-processing unit is designed to generate at least one forecast datum that is representative of an energy expenditure as a function of the input data and of data that are representative of the evolution of at least one exertion parameter.

Thus the rate of heartbeat is an exertion parameter supplied at the input of the data-processing unit. However, the rate of heartbeat may also be a forecast datum when a device according to the invention is suitable to generate forecast data that are representative of the future evolution of the rate of heartbeat. The forecast rate of heartbeat calculated at least from the present (instantaneous) rate of heartbeat is advantageously refined as a function of at least some of the rest of the input data (past rate of heartbeat, position on an itinerary, topology of the remaining route, etc.).

In the same way, predictive calculations of the oxygen saturation of the blood, of the blood pressure, of the body temperature, of the respiratory rate, of the stress, or others, may be envisaged within the context of the invention.

Moreover, advantageously and in accordance with the invention, said data-processing unit is designed to generate at least one forecast datum that is representative of an energy expenditure as a function of the input data and of data that are representative of the evolution of at least one exertion parameter.

A device according to the invention is not restricted to the forecasting of measurable physiological parameters. In fact, the measurement of a set of physiological parameters can enable one or more other parameters relating to the physical (or physiological) state of the subject to be forecast that is/are not measurable, for example the fatigue or the energy reserve of a subject, and that can be represented and/or calculated from various physiological parameters and/or from their evolution over time and therefore from their present and past values.

Certain physiological parameters—amongst which are the rate of heartbeat, the glycaemia, the oxygen saturation of the blood, the blood pressure, the body temperature, the respiratory rate, the conductivity of the skin, and others—may enable, on their own or in combination, a level of fatigue, of energy consumed or of reserves of remaining energy of a subject to be calculated and forecasted and to be compared to a route remaining to be travelled.

In general, in a device according to the invention a user has to provide input data such as, for example, the amount of energy of the subject at the start of the physical exertion.

Furthermore, advantageously and in accordance with the invention, the data-processing unit is designed to compare each exertion parameter to at least one predetermined value, called threshold value, that is specific to said exertion parameter.

In particular, an exertion parameter measured in real time is compared continuously to a threshold value (and/or to a maximum value). Likewise, a calculated exertion parameter (or forecast datum) is also compared to a threshold value in order to avert a possible future exceeding of this threshold value.

Advantageously, for the parameters known as "short-term" parameters—such as the heart rate, for example—which evolve rapidly, the present and forecast data (therefore, short-term) are compared to said threshold values. As far as parameters known as "long-term" parameters—such as the available energy, for example—are concerned, the current value is compared to the forecast made at the start of physical exertion for the whole of the itinerary. For example, it may be considered advantageous to verify that the energy already consumed is not greater than the forecast that had been made at the start of travel for this point of the itinerary, because if that were the case it would mean that the subject is going to have to slow down, or maybe he/she will not have enough energy to reach his/her destination.

A device according to the invention is thus advantageous in order to avert illnesses (cardiovascular, hypoxia, hypoglycaemia, etc.). Such a device is therefore very advantageous for subjects undergoing rehabilitation. Such a device is capable of averting risks before they arise.

Furthermore, advantageously and in accordance with the invention, a device for assisting management of physical exertion includes alarm means activated by at least one forecast datum of at least one exertion parameter outside an interval of predetermined values.

There is nothing to prevent, in a device according to the invention, the interval of values for a certain exertion parameter from being calculated by the device from recorded data. This calculation can be performed before a sequence of physical exertion, after the latter, or it may be updated continuously as a function of the data collected on the subject, enabling the biological, mechanical and/or physiological model(s) for this subject to be refined. However, there is nothing to prevent, either, this interval from being recorded by a user or at the time of manufacture or factory programming of the device. Advantageously, a standard interval is recorded at the time of manufacture, and it is refined after each physical exertion.

A device according to the invention compares, at regular intervals, the forecast of an exertion parameter of the subject to this interval, in order to avert any risk. For example, in the case of the forecast calculation of a glycaemia level the result of this forecast has to be within an interval, and if the level is lower than the minimal value of the interval or greater than the maximal value of the interval the subject is incurring risks that a device according to the invention is suitable to anticipate and to signal to a user with the aid of said alarm means.

The alarm means of a device according to the invention may be of multiple types and, in particular, may use an interface of the device. Thus an alarm may be:
  sonorous, this may be a sound or an audio message, for example,
  optical, this may be a graphical display, colourful, digital or any other means of visual representation deemed appropriate,
  or haptic, this may be a sensation, a vibration or a stinging sensation on a finger, for example.

An alarm according to the invention can be realised in various ways but also, and especially, for various objectives. In fact, if the forecast indicates that an exertion parameter is going to go outside an interval, this information can be used in different ways. A device according to the invention may, for example, emit an alarm if the forecast rate of heartbeat is too slow, but it may also emit an indication of low performance enabling the athletic performance of the subject to be optimised. Likewise, an alarm emitted because a forecast is above an interval may occur because the subject is in danger, or simply because he/she is risking impairing his/her overall performance over the whole of the route.

A device according to the invention may therefore be used both for purposes of training and performance improvement, for example with the objective of improving athletic performance, and for purposes of prevention, for example within the context of postoperative rehabilitation.

Thus an alarm according to the invention extends to assistance devices that are suitable to give advice to the user and/or to the subject, such as to accelerate, to slow down, to retain his/her current speed, in order to keep the exertion parameters within their limits, possibly by optimising the physical performance.

Advantageously, a device according to the invention includes at least one environmental sensor that is suitable to supply data, called environmental data, relating to the environment of the device.

In accordance with the invention, such an environmental sensor may be integrated into the device or may be close by and in communication with said device.

An environmental sensor according to the invention may, for example, measure the ambient humidity, the ambient temperature, the wind, the atmospheric pressure, the level of a particular gas in the atmosphere in which the subject is moving. Numerous other parameters relating to the environment of the subject may advantageously be measured by a device according to the invention.

The invention may also include an atmosphere model giving the conventional levels of gases in the atmosphere, as well as the pressure and the temperature of the latter as a function of the altitude.

Advantageously and in accordance with the invention, the data-processing unit is designed to generate forecast data that are at least partly dependent on said environmental data.

It is advantageous that the data-processing unit is suitable to use data supplied by one or more environmental sensors for the calculation of a forecast of evolution of an exertion parameter.

Indeed, the influence of the environment on the subject may have a very significant impact on some of the future physiological parameters of the subject. The taking into account of certain environmental factors may also be a determining factor for a reliable forecast of these parameters. For example, the respiratory rate and the heart rate depend on the altitude, and compensate for the rise or fall in pressure, in order to maintain an oxygen saturation that is stable or consistent with the level of exertion provided.

Likewise, the expenditures of energy and water are greatly influenced by the surrounding temperature and humidity. Thus the measurement of the external temperature enables the loss of water (high temperature) or the overconsumption of energy in order to maintain body temperature (low temperature) to be estimated. A loss of 2% of the weight of the body during physical exertion, caused by perspiration, is a moderate dehydration but may significantly impair performance.

Furthermore, the energy expenditure of the subject will also be more significant when facing the wind than with his/her back to the wind. The wind may, for example, be taken into account in the energy expenditure (law of resistance proportional to $V^3$, V being the speed). The wind may be a variable that is entered manually by a user (either a single value or a value corresponding to each point or portion of the itinerary to be travelled), measured and/or calculated by the positioning system (atmospheric activities for example, by measurement of the drift), or downloaded prior to the exertion or as the exertion progresses, via communication means.

The envisaged list of sensors relating to the environment of the subject is not exhaustive, and any other sensor deemed necessary for the effective forecasting of an exertion parameter of the subject may be integrated into or connected to a device according to the invention.

The environmental sensors used for each parameter may be of all types and are chosen in accordance with their known advantages and in accordance with the expected characteristics of a device according to the invention.

Additional sensors may be envisaged, in order to improve the forecasts of the device. For example, an accelerometer may be taken on board a vehicle driven by the subject, or may be placed onto the subject himself/herself. In certain situations an accelerometer can enable the position-finding data obtained by GPS to be refined or even replaced. The signals supplied by an accelerometer may also serve to evaluate the level of fatigue of the subject: a subject having undergone repeated and/or intense accelerations within a reduced time-interval risks being more tired.

Furthermore, advantageously and in accordance with the invention, a device for assisting the management of an exertion is suitable to modify and record in a memory, after each exertion, at least one user profile constituted by at least one value that is useful to at least one equation used by the data-processing unit in order to generate forecast data.

Thus certain data relating to the subject can be refined over time with the aid of the accumulation and analysis of data recorded by the device in the course of each physical exertion.

In particular, after each session of exertion such a device can adjust the constants that are useful for making forecasts as a function of the performances actually measured over the itinerary. Likewise, such a device can adjust the limiting thresholds (and/or intervals) for an alarm of certain parameters, in order to enable a device more suited to a particular subject to be obtained.

A device according to the invention is, in particular, designed to be able to record several user profiles and cause them to evolve, a user profile having to be selected prior to each exertion.

A device according to the invention may be capable of refining one or more recorded user profiles. Advantageously, the device refines the constants of the formulae that are used and/or the threshold values (or intervals) for triggering an alarm after each physical exertion.

Thus the values of characteristics specific to the subject that were recorded during itineraries already travelled enable the characteristics defined by default at the time of manufacture, or already individualised characteristics (input data supplied by the user or calculation already performed by the device), to be refined. It is therefore a question of improving and continuously adapting the profile of the subject that has been used to define the forecast values and the programmed values. Thus a user can advantageously update parameters of the profile of a subject with the aid of typical journeys (events and/or specific training), in order to reflect an actual consideration of the evolution of the performances of the subject.

Moreover, a device according to the invention is advantageously designed to generate forecast data for at least two distinct types of physical exertion.

So, in the course of an itinerary a user can, for example, modify the type of physical exertion provided, such as during a triathlon. After having travelled a first itinerary according to a first type of physical exertion, the user can also, for example, reprogram a second itinerary to be travelled, in a second type of exertion different from the first one, and without needing to reconfigure the device or to connect it with another external device such as a personal computer.

Such a device must therefore include, in memory, equations and/or charts of values relating to at least two different types of exertion. The user is then in a position to select, a mode of physical exertion with the aid of at least one interface of the device.

New types of physical exertion can be added to the device by loading files relating to the new type of exertion, in particular new equations (or constants of equations) and/or new charts, into its memories. Advantageously, even when the profile of a subject is recorded for certain types of exertion, the device according to the invention uses this profile in order to improve the forecasts relating to a new type of exertion. The learning of the device is therefore crossed between different types of physical exertion. This is made possible by the fact that the big physiological constants are attached to the subject, not to the type of activity (minimal and maximal heart rate, maximal oxygen saturation, mass, height, etc.).

In addition, a device according to the invention advantageously includes at least one means of communication.

Such a means of communication may equally well be wired or wireless. A wired means of communication can be useful, in particular, for connecting the device to a second device (which may be of any type or may be a second device according to the invention) and loading data into or from the second device.

Thus a device according to the invention may advantageously be connected to a personal computer for further processing of the data recorded by a device for assisting the management of the physical exertion, and/or can load input data onto said device. For example, in accordance with the invention there is nothing to prevent a user from being able to load maps, itineraries, equations and/or charts relating to a type of exertion, user profiles, forecast data relating to exertion parameters over a given itinerary, etc. onto a device according to the invention. Advantageously, such a device is suitable to acquire environmental data such as weather forecasts from an external device such as a personal computer, in particular connected to the Internet.

A wireless means of communication can be used for the same purpose but, in addition, presents other advantages. For example, the positioning device can receive data enabling it to calculate its position; in this case it has a wireless receiver. However, a positioning device according to the invention can also rely on an item of positioning information that is entirely calculated and supplied by an external device with which it is connected by wireless communication. Likewise, information relating to the weather at the point where the subject is located can be communicated by wireless link and directly, which may enable the processing unit to refine its forecasts of exertion parameters; for example, data relating to the speed and direction of the wind, to the temperature, to the humidity, etc.

Moreover, there is nothing to prevent these means of communication from serving to emit an emergency signal when an exertion parameter exceeds a predetermined value, in particular within the context of the rehabilitation of a patient. This embodiment can also be useful, for example, to persons who are known to present a particular health risk, for example cardiovascular frailty.

Lastly, such means of communication can enable a distributed device to be realised on and/or in proximity to the subject.

Moreover, advantageously and in accordance with the invention, a device for assisting the management of the exertion includes a plurality of units which are spatially distributed and connected in a network.

So there is nothing to prevent, furthermore, providing a data-processing unit that is suitable to take into account not only the data of the sensors physically integrated into the device but also data stemming from external sensors. The data-processing unit is, in particular, suitable to process data received from a sensor that has been electrically connected up to the device or is in wireless communication with the latter.

This functionality enables the number of monitored physiological parameters to be extended without increasing the space requirement of a device according to the invention. That also enables great modularity of such a device: only sensors that are useful for one type of exertion in particular are installed on the subject.

Such sensors form part of the portable device according to the invention. Thus a device according to the invention may take the form of a cloud of sensors and/or devices and/or units in a body area network (BAN) on the subject and/or in proximity to the subject.

In particular, a device according to the invention may have a unit in the form of a portable bracelet incorporating, in particular, the positioning device, the data-processing unit, an interface with the user and possibly one or more physiological and/or environmental sensors. The physiological and/or environmental sensor(s) may be distributed on or in proximity to the subject. For example, the respiratory rate of a subject is advantageously measured with the aid of a sensor arranged around the chest of the subject, which is not necessarily compatible with the ease of use and the visual interface arranged in a bracelet. The two elements of such a device according to the invention are therefore connected by a wired or wireless connection.

The invention extends to a device for assisting the management of the exertion, characterised in combination by some or all of the characteristics mentioned above or below.

BRIEF DESCRIPTION OF THE DRAWINGS

Other characteristics, objects and advantages of the invention will become apparent from the detailed description which follows with reference to the drawings which represent, by way of non-limiting example, a preferred embodiment. In these drawings:

FIG. 4 is a schematic representation of the instantaneous past measurements of exertion parameters over a first portion of an itinerary, and of forecast and programmed values for these exertion parameters calculated for a device according to the invention, during a foot-race.

DETAILED DESCRIPTION OF THE PREFERRED EMBODIMENTS

In a particular embodiment described below and represented in the Figures, a device according to the invention for assisting the management of a physical exertion is adapted so that the user and the subject are the same human being.

Such a device has a part in the form of a bracelet that is advantageously capable of being worn on the wrist, on the arm or on the ankle.

Figure 1:
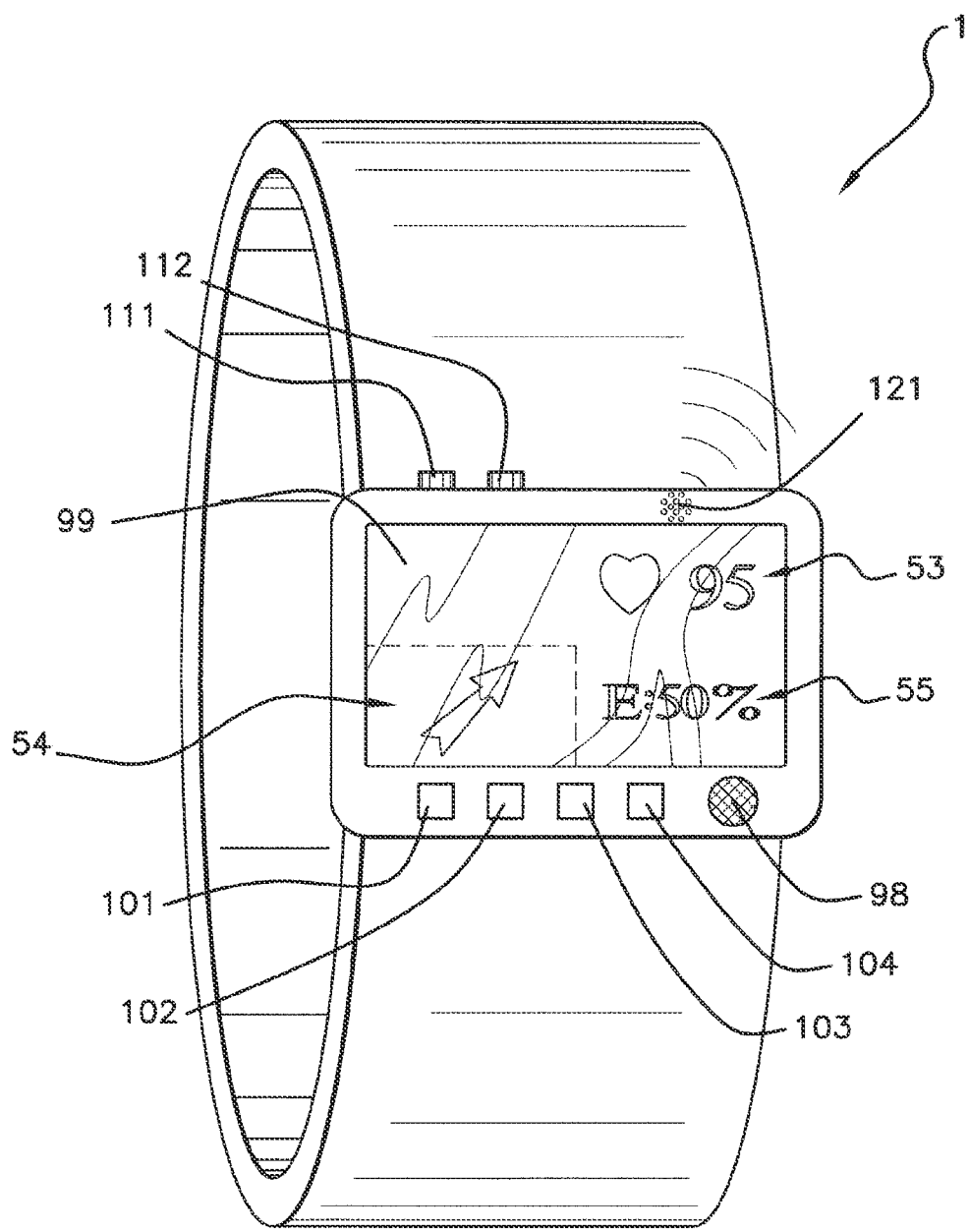
FIG. 1 is an external schematic representation of a bracelet of a portable device according to the invention.
Figure 2:
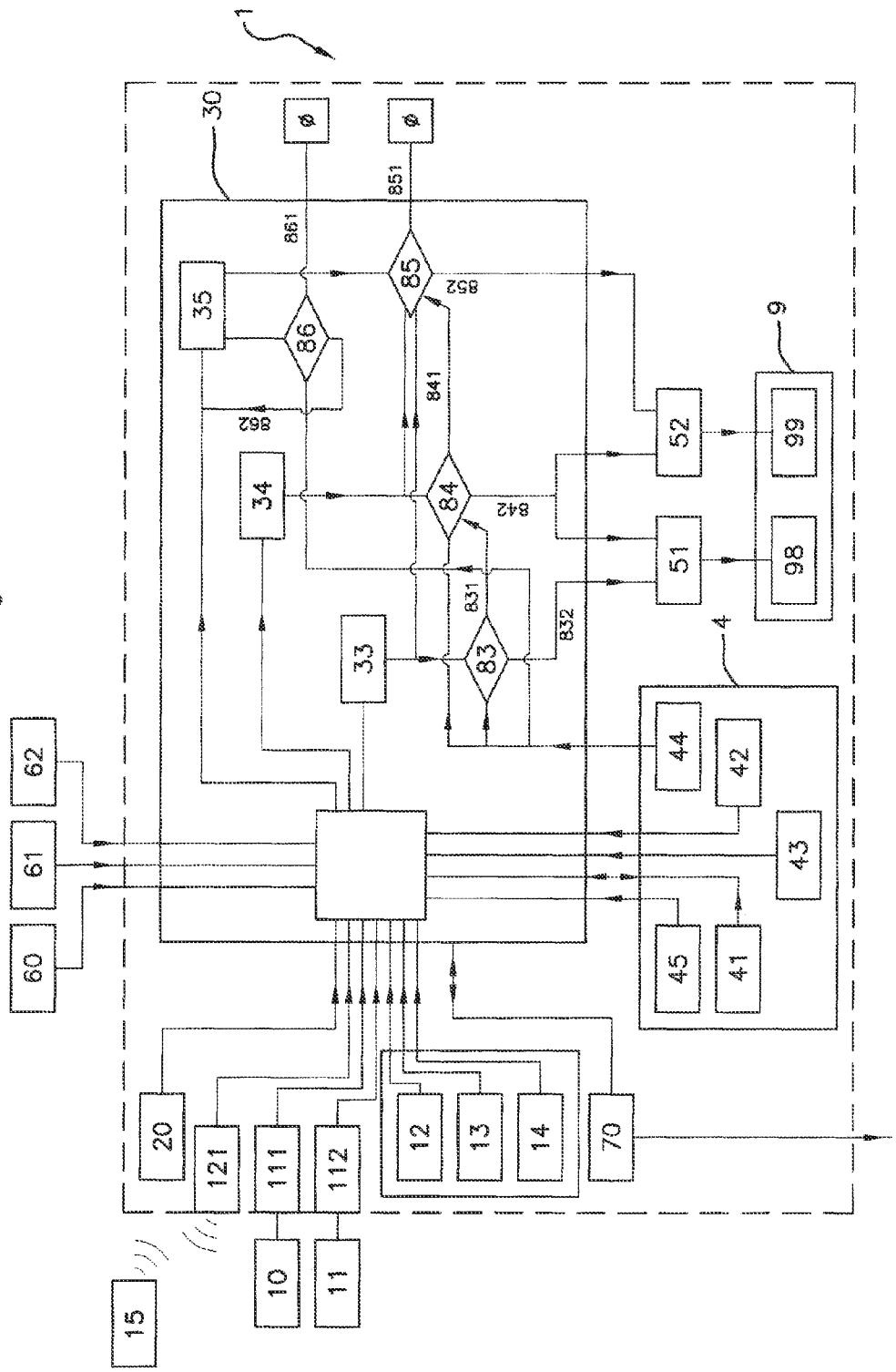
FIG. 2 is a schematic representation of an embodiment of a device according to the invention, illustrating the input/output relationships between certain component elements of the device according to the invention.

The bracelet has, viewed from the outside, a screen 99 and a loudspeaker 98, and buttons 101 to 104 (which could advantageously be replaced or supplemented by a tactile interface) in order to interact with the user. Such a device may, for example, display on the screen 99 a measured value 53 of the rate of heartbeat (in FIG. 1, 95 beats per minute), a calculated value 55 of the percentage of energy available at the start already consumed (in FIG. 1, 50% of energy consumed), and an indicator relating to an advice message 54 (in FIG. 1, an arrowed symbol directed upwards in order to indicate to the user to accelerate).

In addition, this bracelet has ports 111, 112 for wired connection and a port 121 for wireless connection, in order to be able to connect sensors or devices or units of a portable device for assisting the management of an exertion according to the invention to the bracelet so as to form a portable device distributed in the form of a network on the body of (or in proximity to) the subject.

Furthermore, such a bracelet of a portable device according to the invention includes:
 a unit 20 for receiving GPS (Global Positioning System) signals and calculating a position in latitude, longitude and altitude,
 a data-processing unit 30,
 at least one memory 4.

The portable device according to the invention also includes at least one sensor 10 for heart rate, a sensor 11 for oxygen saturation of the blood, and a sensor 12 for body temperature, which may be arranged in the bracelet or elsewhere on the body of the subject and in communication with said bracelet. For example, the sensor 10 for heart rate may be arranged on the chest of the subject and connected to the bracelet by means of the wired port 111; the sensor 11 for oxygen saturation of the blood may be arranged on a finger of the subject and connected to the bracelet by means of the wired port 112; and the sensor 12 for body temperature may be arranged in the portable bracelet, on the side of the bracelet that is intended to be in contact with the skin of the subject.

A device 1 according to the invention may also include a sensor 15 for respiratory rate, external to the bracelet, for example suitable to be arranged around the chest of the subject and suitable to be able to communicate in wireless manner with the bracelet via the port 121 for wireless connection.

In this embodiment of the invention the device for assisting the management of the exertion also includes environmental sensors: a sensor 13 for external temperature and a sensor 14 for atmospheric pressure.

The data—such as itinerary 60 (coordinates of the point of departure and coordinates of the point of arrival), energy 61 available prior to the exertion, and type 62 of physical exertion—are entered manually by a user prior to the start of the exertion. The data-processing unit is suitable to store these input data, at least for the duration of the exertion, in a memory 41.

Moreover, the data received from the physiological sensors 10, 11, 12 and environmental sensors 13, 14, as well as the positioning data, are communicated in real time to the data-processing unit 30.

Thus the data-processing unit 30 retrieves from one or more memories 42, 43 the equations and charts to be applied to the data received directly as a function of the type of exertion. Starting from said data, the processing unit is suitable to provide forecast data in the form of objectives (programmed values) relating to the whole of the itinerary remaining to be travelled, and forecast data in the form of a short-term forecast (forecast data).

At regular time-intervals the data-processing unit performs a comparison 83 between the values of the physiological data 33 measured by the physiological sensors 10, 11, 12 and limiting values (capable of forming one or more ranges) which it accesses in a memory 44. If a measured value 33 exceeds or is less than a limiting value (link 832), an alarm message 51 is emitted by the data-processing unit in order to be transmitted to the user via at least one interface 9, for example by means of a loudspeaker 98.

If no measured value 33 exceeds or is less than a limiting value 44 (link 831), the data-processing unit performs a comparison 84 between the forecast values 34 and the same limiting values 44.

If at least one forecast value 34 exceeds or is lower than a limiting value 44 (link 842), for example the forecast heart rate FCP of FIG. 4, an alarm message 51 is emitted and is transmitted to a user via at least one of the interfaces 98, 99.

If all of the forecast values 34 lie within the ranges of limiting values 44 (link 841), the data-processing unit performs a comparison 85 between measured values 33 and programmed values 35 and a comparison 85 between forecast values 34 and the same programmed values 35. If the result of the comparison 85 indicates that the measured values 33 and the forecast values 34 correspond to an error percentage around the programmed values 35 (link 851), the data-processing unit 30 continues its passive surveillance. If the measured values 33 and/or forecast values 34 are below or above the programmed values 35 (link 852), the data-processing unit 30 emits an advice message 52 which is transmitted to the user by means of, for example, a screen 99, being expressed for a user by a visual indication 54.

Furthermore, prior to the start of the physical exertion, once the programmed values have been calculated a comparison 86 between the programmed values of heart rate over the whole of the itinerary and a range constituted by a minimal value $FC_{min}$ and by a maximal value $FC_{Max}$ (limiting values 44) of the heart rate of the subject is then performed. The limiting values 44 forming a range are recorded in a memory 4 of the device 1. They can be entered manually by a user or calculated as a function of other parameters provided, or not, by the user. For example, $FC_{min}$ and $FC_{Max}$ can be calculated from the height, age and weight of the individual.

If the result of the comparison 86 indicates that at least one value of the programmed values 35 of the heart rate is below $FC_{min}$ or above $FC_{Max}$ (link 862), the programmed values are recalculated until the programmed values 35 of the heart rate satisfy this criterion. If the result of the comparison 86 indicates that the programmed values 35 of the heart rate are within the limits of the range [$FC_{min}$; $FC_{Max}$] (link 861), the device validates and retains these programmed values 35.

Figure 3:
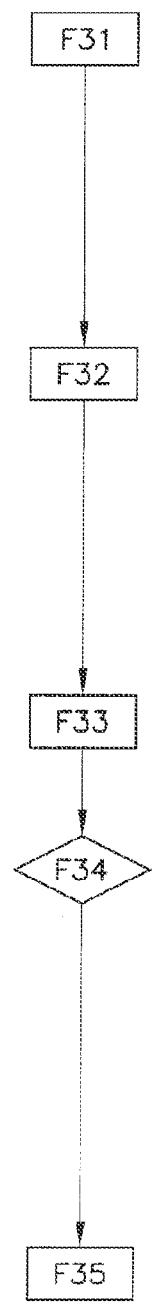
FIG. 3 is a schematic representation illustrating examples of programmed values of speed, heart rate and remaining energy as a function of the topology of an itinerary prior to the start of a physical exertion of running type on this itinerary, said values being calculated by a device according to the invention.
Figure 3:
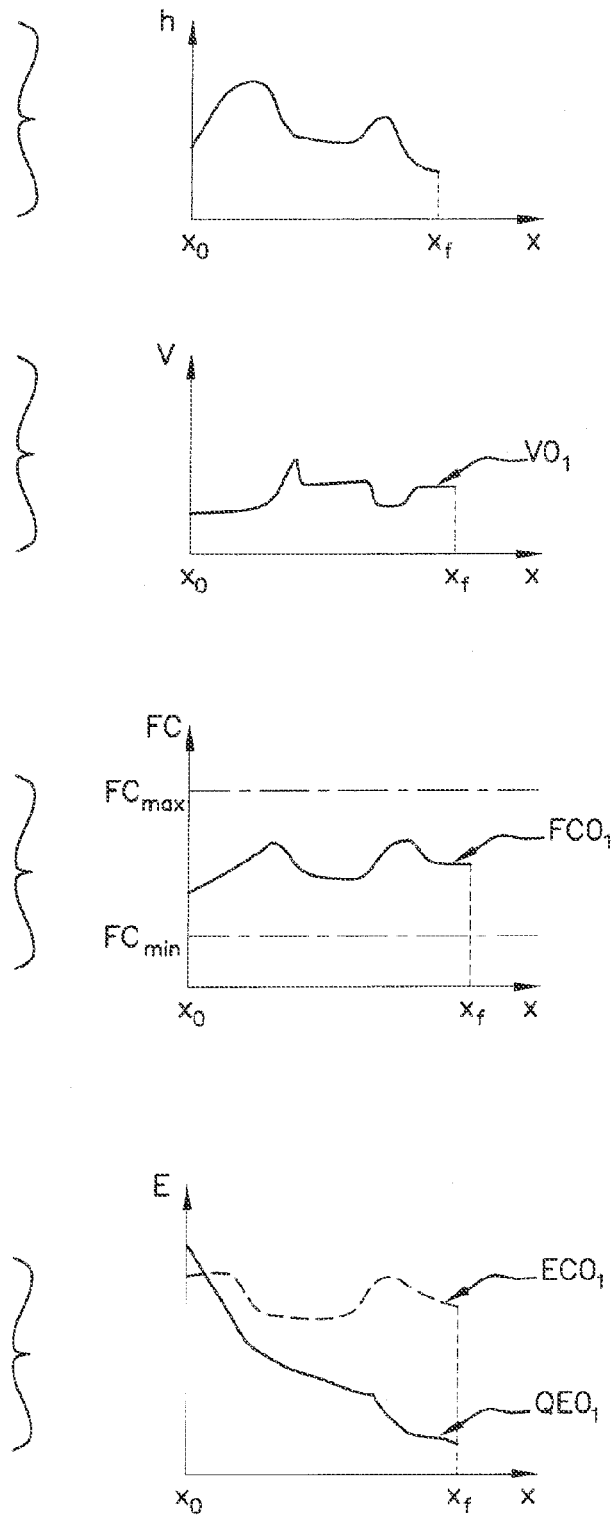

In the example presented in FIGS. 3 and 4 the type of physical exertion is a foot-race in which the subject is a human being who is also the user of the device.

FIG. 3 presents the programmed values for the whole of the itinerary, calculated prior to the start of the race, which correspond to performance objectives. In FIGS. 3 and 4, h represents the altitude at each point x of the itinerary between the point of departure $X_0$ and the point of arrival $X_f$, V represents the speed as a function of the same abscissas (x), FC represents the heart rate, and E the energy.

In particular, in FIG. 3, $VO_1$ represents the programmed values of the speed of the subject at each point x of the itinerary. $FCO_1$ represents the programmed values of the heart rate of the subject at each point x of the itinerary. $ECO_1$ represents the programmed values of the instantaneous consumed energy at each point of the itinerary, and $QEO_1$ the programmed values of the amount of energy remaining for the subject at each point x of the itinerary.

In step F31 the user provides as input datum an itinerary 60 to be travelled, either by entering a point of destination starting from his/her current position, or between two positions $X_0$ and $X_f$. With the aid of the maps 45 prerecorded in one or more memories 4, the assistance device is designed to realise a topographical representation of the itinerary.

From this topographical representation, in step F32 the device implements the process, in the course of which it generates programmed values 35—that is to say, over the whole of the itinerary—of the speed $VO_1$ of the subject at each point of the itinerary. Any point x of the itinerary corresponds to a time t of the race, once the programmed values of the speed $VO_1$ have been calculated.

In the same way, in step F33 the device generates programmed values 35 of the heart rate $FCO_1$ of the subject. The device can realise this forecast of heart rate $FCO_1$ from the speed $VO_1$, and possibly from the environmental parameters (wind, temperature, . . . ). This forecast $FCO_1$ can, in particular, be realised from chart(s) 43 (the chart(s) 43 may be personalised to a particular subject in the course of an exertion test, for example).

In step F34 the device performs a comparison 86 ($FC_{min} \leq FC \leq FC_{Max}$) between programmed values 35 of the heart rate and the limiting values 44, $FC_{min}$ and $FC_{max}$. If at least one of the programmed values 35 is not within this range, the profile $FCO_1$ is adjusted—that is to say, the programmed values of the heart rate are modified until they satisfy this criterion.

The device then makes a forecast of energy consumed, and therefore a forecast of remaining consumable energy, on condition that a user has provided the consumable energy stored by the subject as input datum 61. The consumable energy 61 is constituted by the energy that is going to be available for the physical exertion envisaged over the envisaged itinerary; that is to say, generally fast sugars and slow sugars, sometimes certain fats.

In step F35 the device realises a long-term forecast (calculation of programmed values 35) of the energy consumption $ECO_1$ of the subject (and therefore of the remaining amount of energy $QEO_1$). For example, an equation enabling this forecast to be made is (equation (1)):

$$\int_{x=X_0}^{x=X_f} \left( \frac{1}{2}mV(x)^2 + mg \cdot dh(x) \right) \cdot dx = E(X_0 \to X_f)$$

Where m is the mass of the subject, g is the acceleration due to gravity, V(x) is the speed of the subject in absolute value at a point x of the itinerary, dh(x) is the difference in height travelled at point x of the itinerary, and $E(X_0 \to X_f)$ is the total energy expended by the subject over the whole of the itinerary (from $X_0$ to $X_f$). $E(X_0 \to X_f)$ is the programmed value of the energy consumed at point $X_f$, that is to say, $E(X_0 \to X_f) = ECO_1(X_f)$.

Ideally, the remaining energy of the subject at any point of the itinerary is very close to the amount of energy forecasted at this point. In particular, at the end of the physical exertion a user may aim at a remaining amount of energy of the subject close to zero, which means that he/she has used the maximum of his/her energy potential over this itinerary in the course of the physical exertion.

If the remaining consumable energy of the subject is less than or equal to zero before the end of the itinerary, this means that he/she will not be able to reach the end of the itinerary, and certain objectives must therefore be revised down, in particular the objectives relating to speed of travel over the itinerary.

On the other hand, over a very short itinerary, for example, and in order to remain within the limits of safety (in particular, a heart rate lower than $FC_{Max}$), it may happen that all the consumable energy cannot be consumed over the itinerary.

In FIG. 4 the subject has already travelled a portion of the itinerary ($X_0$ to $X_t$).

At step F41, at a time t the device acquires its position and performs a comparison 85 of the measured values 33 (measured speed $V_m$, measured heart rate $FC_m$) from $X_0$ to $X_t$ to the objectives ($VO_1$, $FCO_1$) established prior to the start of the physical exertion.

Step F42 represents the measurement of the speed $V_m$ of the subject from $X_0$ to $X_t$; this measurement is necessary for the calculation of the energy consumed by the subject, performed in step F45.

Likewise, step F43 represents the measurement of the heart rate $FC_m$ of the subject from $X_0$ to $X_t$; this measurement is necessary for the calculation of the forecast values 34 of the heart rate (FCP), performed in step F44.

In the example of FIG. 4 the subject has gone faster than programmed ($V_m$ is above $VO_1$), and his/her heart rate is consequently much higher than programmed ($FC_m$ above $FCO_1$), although it remains lower than $FC_{Max}$ between $X_0$ and $X_t$.

In the course of step F44, from the recorded data ($V_m$, $FC_m$) between $X_0$ and $X_t$, from the programmed long-term values 35 of race speed ($VO_1$), and from the topology of the itinerary to come, the device generates forecast short-term values 34 of the heart rate (FCP) over a time horizon Δ.

In the course of step F441 these forecast short-term values 34 (FCP) are compared 84 to the predetermined limiting values 44 of heart rate for this subject ($FC_{min}$ and $FC_{Max}$), and the comparison 84 indicates that the heart rate is going to exceed the limiting value $FC_{Max}$ (FCP≥$FC_{max}$), therefore the conditions of the comparison 84 are not fulfilled (842), and the data-processing unit of the device emits a slow-down advice message 52 to the user by means of, for example, the screen 99.

At step F441, since one of the conditions ($FC_{min} \leq FC \leq FC_{Max}$; $FC_{min} \leq FCP \leq FC_{Max}$) is not met, step F46 is initiated (path 446).

At step F45, since the speed $V_m$ of the subject is higher than programmed on the first travelled portion of the itinerary, the device calculates that the energy actually consumed $EC_r$ is more significant than the forecast $ECO_1$, and therefore the energy actually remaining $QE_r$ is decreasing more rapidly. Therefore if the subject maintains a speed greater than or equal to the programmed values 35, he/she will not be in a position to reach $X_f$, since his/her reserve of consumable energy will be zero before he/she reaches $X_f$.

A new profile of programmed values 35 has to be established in order to avoid the exceeding of $FC_{Max}$ and in order to enable the subject to conserve energy up until $X_f$.

In order to calculate the energy consumed as a function of the speed, of the topography, and/or of the environmental parameters (wind, for example), the portable device for assisting the management of the physical exertion uses, for example in the case of a runner, an equation, recorded in a memory 42, of the following type (equation (2)):

$$Ref \int_{t=T}^{t=T+\Delta}(P_{running}+P_{ht.diff.}+P_{air}).t.dt=E(\Delta)$$

Indeed, at any instant the balance of forces exerted on the subject can be written as:

$$m.a=F_{running}+F_{ht.diff.}+F_{air}$$

With: a, the instantaneous acceleration of the subject $$F_{running}=m.g.Cr$$

$$F_{ht.diff.}=m.g.\sin(p(t))$$

$$F_{air}=\tfrac{1}{2}.\rho(t).S.Cx.V(t)^2$$

from which, with the relationship $P(t)=\vec{F}(t).\vec{V}(t)$ $$P_{running}=m.g.V(t).Cr$$

$$P_{ht.diff.}=m.g.V(t).\sin(p(t))$$

$$P_{air}=\tfrac{1}{2}.\rho(t).S.Cx.V(t)^3$$

Where V(t) is the speed of the subject in absolute value at a time t, $\Delta$ is the period elapsed since a time T at which the calculation is performed—that is to say, the time horizon of the forecasts—and $E(\Delta)$ is the energy expended by the subject during the period $\Delta$.

The coefficients m (mass), Cr (coefficient of specific friction of the runner (of his/her soles) and in the condition of the road), S (apparent surface), Cx (drag coefficient) and Re (energy output) can be personalised to a particular subject. To do this, the user can enter said coefficients manually. Alternatively or in supplement, these coefficients specific to the subject can be refined automatically by the device after each session of physical exertion carried out by the subject. The device adjusts these coefficients by inverting the calculation previously performed and starting from the speeds actually measured at the time of travel of the itinerary by the subject. The coefficients p(t) (average gradient at a time t), g (acceleration due to gravity) and $\rho(t)$ (density of the air at time t, corresponding to a point x of given altitude) are data 41 recorded in the memory 4.

At step F46 the device therefore establishes a new, more modest, profile of programmed values 35 of speed ($VO_2$), which will be the reference speed profile for the rest of the itinerary.

Then, at step F47 the device establishes a new profile of programmed values 35 of the heart rate $FCO_2$, based on the new, more modest, profile $VO_2$ which will be the reference speed profile for the rest of the itinerary.

Then the device repeats step F441, in order to verify that the new speed profile $VO_2$ is compatible with a heart rate $FCO_2$ lying within the range of $FC_{min}$ and $FC_{max}$.

Steps F46, F47, F441 are repeated in this order until the criteria applied in step F441 are fulfilled. The device then passes (path 448) to step F48.

At step F48 the device establishes a new profile of programmed values 35 of the energy consumed $ECO_2$, in particular from the new profile $VO_2$ which will be the reference speed profile for the rest of the itinerary. Said device also establishes a new profile of programmed values 35 of the remaining amount of consumable energy $QEO_2$ from the values $ECO_2$.

Then, at step F481 the device verifies that none of the programmed values 35 of the amount of energy $QEO_2$ is equal to zero before the subject reaches $X_f$. If the amount of programmed remaining energy reaches zero before position $X_f$, the device establishes a new speed profile that is compatible with this criterion (passage to step F46 by path 486).

If the criterion of step F481 is satisfied, the device terminates this series of steps (path 480).

The device repeats steps F41 to F481 at predetermined time-intervals.

The other measured parameters enable the calculations of heart rate and of energy consumed to be refined. Thus the oxygen saturation of the blood has an influence on the physical performance and therefore on the heart rate. Likewise, the temperature of the body or the hydration state of the subject have an influence on the physical performance. For example, a 1% loss of water leads to the first signs of reduction of performance.

The environmental parameters such as external temperature and atmospheric pressure also have an influence on parameters such as the heart rate and the oxygen saturation of the blood, and they are at the root of modifications of performance (cf. for example, "Précis de physiologie de l'exercice musculaire", Per-Olof Åstrand and Kaare Rodahl, Editions Masson, $3^{rd}$ edn., 1994). For instance, altitude (low partial pressure of oxygen) limits performance. Likewise, a high temperature acts as upper bound of energy consumption.

Furthermore, such a device according to the invention has means 70 for communication with an external device. Such means 70 of communication can enable the device to be connected to a personal computer which enables files to be loaded in one direction or another between the device and the computer. For example, historical records of data and of the profiles of users can be uploaded from the device to the computer, and data relating to an itinerary (maps, topology, meteorological conditions, etc.) can be downloaded from the computer to the device.

The invention may form the subject of numerous other embodiment variants which are not represented.

In particular, the set of the equations that have been presented results from biological, biomechanical and/or physiological studies, and they are only cited as examples. Any other equation deemed more appropriate or more exact can be used in a device according to the invention. They may, for example, be implemented by neural networks.

Likewise, the logical steps that have been presented are given by way of example of a particular embodiment, and they may be realised in different logical orders.

Moreover, the measured physiological parameters can be chosen in accordance with the subject, in accordance with the type of exertion (type of sport, rehabilitation, competition, etc.), and may include other parameters which are deemed useful but which have not been presented amongst the examples cited above. The exertion parameters, the evolution of which a device according to the invention is suitable to forecast in more or less the short term, may also be more numerous than those presented.

Furthermore, in a device according to the invention there is nothing to prevent numerous other environmental parameters that are determining factors for the physical exertion being carried out from being taken into account: the surface condition of a terrain, dangerousness, etc.

Moreover, since a device according to the invention is intended to be used outdoors, and possibly for physical exertions such as swimming, it is advantageously impervious to water.

The invention claimed is:

1. Portable device (1) for assisting the management of a physical exertion provided by a subject, comprising:
    at least one sensor (10, 11, 12) for a at least one physiological parameter, called exertion parameter, evolving as a function of the physical exertion, said sensor being suitable to provide digital data, called exertion data, that are representative of said exertion parameter,
    at least one device, called positioning device (20), that is suitable to determine its own position in a given topographical frame of reference and to provide digital data, called positioning data, that are representative of this position,
    at least one interface (98, 99) for communication with a user,
    at least one memory (4) in which data, called input data, are capable of being recorded, comprising at least:
    positioning data provided by said positioning device, exertion data,
    data that are representative of an itinerary to be travelled in said topographical frame of reference by said subject in the course of the physical exertion,
    at least one data-processing unit (30), designed:
        to use said input data at any present point of the itinerary, said input data comprising at least topographic data of a part of the itinerary remaining to be travelled by the subject from the present point, to generate data, called forecast data, that are representative of the evolution of at least one of said exertion parameter over all of the itinerary, from equations and from tables of values recorded in at least one memory of the device,
        to compare these forecast data with predetermined values recorded in at least one memory of said assistance device,
        to generate data that are representative of a message, the content of which is a function of the result of the comparison of the forecast data and the predetermined values,
        to transmit said data that are representative of a message to the interface, with a view to the communication of said message to a user.

2. Device as claimed in claim 1, wherein a first exertion parameter is the heart rate and at least one second exertion parameter is chosen from: the oxygen saturation of the blood, the body temperature, the level of glucose in the blood, the blood pressure, the respiratory rate, the conductivity of the skin.

3. Device as claimed in claim 1, wherein said data-processing unit (30) is designed to generate said forecast data that are representative of the evolution of the exertion parameters as a function of the input data.

4. Device as claimed in claim 1, wherein said data-processing unit (30) is designed to generate at least one forecast datum that is representative of an expenditure of energy as a function of the input data and of data that are representative of the evolution of at least one exertion parameter.

5. Device as claimed in claim 1, wherein said data-processing unit (30) is designed to compare each exertion parameter to at least one predetermined value, called threshold value, that is specific to said exertion parameter.

6. Device as claimed in claim 1, including alarm means activated by at least one forecast datum of at least one exertion parameter outside a range of predetermined values.

7. Device as claimed in claim 1, including at least one environmental sensor (13, 14) that is suitable to provide data, called environmental data, relating to the environment of the device.

8. Device as claimed in claim 7, wherein the data-processing unit (30) is designed to generate said forecast data that are at least partly dependent on said environmental data.

9. Device as claimed in claim 1, wherein the device is suitable to modify and record in a memory (4), after each exertion, at least one user profile constituted by at least one value that is useful for at least one equation used by the data-processing unit (30) in order to generate said forecast data.

10. Device as claimed in claim 1, wherein the device is designed to generate said forecast data for at least two distinct types of physical exertion.

11. Device as claimed in claim 1, wherein the device has at least one means (70) of communication.

* * * * *